United States Patent [19]

Gray et al.

[11] Patent Number: 5,447,841
[45] Date of Patent: Sep. 5, 1995

[54] METHODS FOR CHROMOSOME-SPECIFIC STAINING

[75] Inventors: Joe W. Gray, Livermore; Daniel Pinkel, Walnut Creek, both of Calif.

[73] Assignee: The Regents Of The Univ. Of California, Oakland, Calif.

[21] Appl. No.: 627,707

[22] Filed: Dec. 14, 1990

Related U.S. Application Data

[63] Continuation of Ser. No. 937,793, Dec. 4, 1986, abandoned, which is a continuation-in-part of Ser. No. 819,314, Jan. 16, 1986, abandoned.

[51] Int. Cl.$^6$ .............................................. C12Q 1/68
[52] U.S. Cl. ........................................ 435/6; 435/243;
435/805; 435/820; 436/501; 436/63; 436/64;
536/22.1; 536/23.1; 536/24.3; 536/24.31;
536/24.32; 536/25.42; 935/77; 935/78
[58] Field of Search ................... 435/6, 91, 91.1, 91.2,
435/5, 243, 805, 820; 436/501, 504, 63, 64;
536/27, 22.1, 23.1, 24.3-24.33, 25.42; 935/23,
78, 77

[56] References Cited

U.S. PATENT DOCUMENTS

| | | | |
|---|---|---|---|
| 4,358,535 | 11/1982 | Falkow et al. | 435/5 |
| 4,647,529 | 3/1987 | Rodland et al. | 435/6 |
| 4,681,840 | 7/1987 | Stephenson et al. | 435/6 |
| 4,683,195 | 7/1987 | Mullis et al. | 435/6 |
| 4,707,440 | 11/1987 | Stavrianopoulos | 435/6 |
| 4,710,465 | 12/1987 | Weissman et al. | 435/91 |
| 4,711,955 | 12/1987 | Ward et al. | 536/29 |
| 4,721,669 | 1/1988 | Barton | 435/6 |
| 4,725,536 | 2/1989 | Fritsch et al. | 435/6 |
| 4,770,992 | 9/1988 | Van den Engh et al. | 435/6 |
| 4,772,691 | 9/1988 | Herman | 536/27 |
| 4,888,278 | 12/1989 | Singer et al. | 435/6 |

FOREIGN PATENT DOCUMENTS

| | | |
|---|---|---|
| 2019408 | 10/1979 | United Kingdom . |
| 2215724 | 9/1989 | United Kingdom . |
| 8705027 | 8/1987 | WIPO . |
| 9005789 | 5/1990 | WIPO . |

OTHER PUBLICATIONS

Pinkel et al. (1986) Proceedings of the Nat'l Acad Sci (USA) vol. 83, pp. 2934–2938.
Ardeshir et al. (1983) Mol. & Cell. Biology, vol. 3, No. 11, pp. 2076–2088.
Fisher et al. (1984) Proceedings of the Nat'l Acad Sci (USA) vol. 81, pp. 520–524.
Weiss et al. (1984) Nature, vol. 310, pp. 650–655.
Litt et al. (1985) Proceedings of the Nat'l Acad Sci (USA) vol. 82, pp. 6206–6210.
Yunis et al. (1977) Chromosoma, vol. 61, pp. 335–344.
Langer-Safer et al. (1982) Proc. Nat'l Acad Sci (USA) vol. 79, pp. 4381–4385.
Montgomery et al. (1983) Proc. Natl Acad Sci (USA) vol. 80, pp. 5724–5728.
Lewin, B. (editor), Genes (2nd Edition John Wiley & Sons, Inc. 1984) pp. 298–294 and pp. 464–465.
Gray et al., (Abstract) "Flow Cytometric Detection of Chromosome Aberrations"; *Conference on Flow Cytometry in Cell Biology and Genetics*, Jan. 15–17, 1985 (San Francisco, Calif.).
Szabo and Ward, *TIBS*, 7(11): 425–427 (Dec. 1982).
Gall and Pardue, *PNAS* (USA), 63: 378–383 (1969).
Buongiorno-Nardelli and Amaldi, *Nature*, 225: 946–948 (1970).
John et al. *Nature*, 223: 582–587 (1969).
Schardin et al., *Hum. Genet.*, 71: 281–287 (1985).
Durnam et al., *Som. Cell Molec. Genetics*, 11(6): 571–577 (1985).
Manuelidis, *Hum. Genet.*, 71: 288–293 (1985).

(List continued on next page.)

*Primary Examiner*—Margaret Parr
*Assistant Examiner*—Ardin H. Marschel

[57] ABSTRACT

Methods and compositions for chromosome-specific staining are provided. Compositions comprise heterogenous mixtures of labeled nucleic acid fragments having substantially complementary base sequences to unique sequence regions of the chromosomal DNA for which their associated staining reagent is specific. Methods include methods for making the chromosome-specific staining compositions of the invention, and methods for applying the staining compositions to chromosomes.

17 Claims, 1 Drawing Sheet

OTHER PUBLICATIONS

Herzenberg et al., *PNAS* (USA), 76 (3): 1453–1455 (Mar. 1979).
Britten et al., *Methods of Enzymology*, 29: 363–418 (1974).
Benton and Davis, *Science*, 196: 180–182 (1977).
Landegent et al., *Nature*, 317: 175–177 (12 Sep. 1985).
Olsen et al., *Biochemistry*, 19: 2419–2428 (1980).
Schmeckpeper et al., *Proc. Natl. Acad. Sci. USA* 76(12): 6525–6528 (1979).
Brison et al., *Molecular and Cellular Biology*, 2 (15): 578–587 (1982).
Manuelidis and Ward, *Chromosoma (Berl.)* 91: 28–38 (1984).
Lawrence Livermore National Laboratory publication, *Energy and Technology Review*, Jul. 1985, pp. 82–83 entitled "Chromosome—Specific Human Gene Libraries".
Van Dilla and Deaven (Abstract), *Am. J. of Human Genetics*, 37 (R Supplement) (Jul. 1985).
Lewin, R., *Science*, 221 (4616): 1167 (16 Sep. 1983).
Albertson, *EMBO J.*, 4 (10): 2493–2498 (1985).
Albertson, *EMBO J.*, 3 (6): 1227–1234 (1984).
Cox et al., *Developmental Biology*, 101: 485–502 (1984).
Sealy et al. *Nucleic Acid Research*, 13: 1905–1922 (1985).
Harper and Saunders, *Chromosoma (Berl)* 83: 431–439 (1981).
Wallace et al., *Nucleic Acids Research*, 9 (4): 879–894 (1981).
Scalenghe et al., *Chromosoma* (Berl.), 82: 205–216 (1981).
Jabs et al., *PNAS* (USA), 81: 4884–4888 (1984).
Stewart et al., *Nucleic Acids Research*, 13(11): 4125–4132 (1985).
Landegent et al., *Exp. Cell Res.*, 153: 61–72 (1984).
Cannizzaro et al., *Cytogenet. Cell Genet.* 39: 173–178 (1985).
Kao et al., *Human Genetics*, 62: 337–341 (1982).
Harper and Saunders, *PNAS*, 78: 4458–4460 (1981).
Willard et al., *Nucleic Acids Res.*, 11: 2017–2033 (1983).
Manuelids, *PNAS (USA)*, 81: 3123 (1984).
Rappold et al., *Human Genetics*, 67: 317 (1984).
Cantor and Schimmel, *Biophysical Chemistry: The Behavior of Biological Macromoles* (Part III, p. 1228) (Freeman 1980).
Thompson et al, *Thompson & Thompson: Genetics in Medicine*, 5th ed., W. B. Saunders Co., Philadelphia, Pa., pp. 38–39 (1991).
Leroy E. Hood et al, *Molecular Biology of Eucaryotic Cells*, W. A. Benjamin, Inc., Menlo Park, Calif., pp. 47–51 (1975).
J. E. Landegent, et al, "Use of Whole Cosmid Cloned Genomic Sequences for Chromosomal Localization by Non-Radioactive In Situ Hybridization," *Human Genetics*, 77:366–370 (1987).
"Detection of DNA Sequences in Nuclei in Suspension by In Situ Hybridization and Dual Beam Flow Cytometry" (UCRL 93372 Abstract) Trask, B., et al—Analytical Cytology X Conference, Hilton Head Resort, Hilton Head Island, S.C., Nov. 17, 1985–Nov. 22, 1985.
"Cytogenetics Using Fluorescent Nucleic Acid Probes and Quantitative Microscopic Measurement" (UCRL 93269 Abstract) Pinkel, D., et al—Analytical Cytology X Conference, Hilton Head Resort, Hilton Head Island, S.C., Nov. 17, 1985–Nov. 22, 1985.
"Rapid Quantitative Cytogenic Analysis Using Fluorescently Labeled Nucleic Acid Probes", (UCRL 93553 Abstract), Pinkel, D., et al, U.S.–Japan Joint Environmental Panel Conf., Research Triangle Park, N.C., Oct. 21, 1985–Oct. 23, 1985.
"Chromosome Translocation of Low Radiation Doses Quantified Using Fluorescent DNA Probes", (UCRL 93837 Abstract), Straume, T., et al, Radiation Research Society Meeting, Las Vegas, Nevada, Apr. 12, 1986–Apr. 17, 1986.
"Rapid Translocation Analysis Using Fluorescence In Situ Hybridization: Applied to Long Term Biological Dosimetry", (UCRL 102265 Abstract), Lucas, J. N., et al, Radiation Research Meeting, New Orleans, Louisiana, Apr. 7, 1990–Apr. 12, 1990.
"Detection of Structural and Numerical Abnormalities in Metaphase Spreads and Interphase Nuclei Using In Situ Hybridization", Pinkel, D., et al, *Cancer Genet. and Cytogenet.* (UCRL 101043 Abstract) 41:236 (Oct. 1989).
"Flow Cytometric Detection of Chromosome Aberrations," (Abstract) Gray et al, Conference on Flow Cytometry in Cell Biology and Genetics, Clift Hotel, San Francisco, California, Jan. 15, 1985–Jan. 17, 1985.
"Simplified Cytogenetics Using Biotin Labeled Nucleic Acid Probes and Quantitative Fluorescence Microscopy," (UCRL 93243 Abstract), Pinkel et al, *American Journal of Human Genetics* (Supplement), 37:A112, Jul. 1985.

OTHER PUBLICATIONS

"Detection of Translocations and Aneuploidy in Metaphase Spreads and Interphase Nuclei by In Situ Hybridization with Probes Which Stain Entire Human Chromosomes," (UCRL 101042 Abstract) Pinkel et al, 21st Oak Ridge Conference on Advanced Conepts in the Clinical Laboratory, Apr. 13, 1989–Apr. 14, 1989.

"Colony Hybridization: A Method for the Isolation of Cloned DNAs That Contain A Specific Gene," Grunstein et al, *PNAS, USA*, vol. 72, No. 10, Oct. 1975, pp. 3961–3965.

"Heterogeneity of Chromosome 22 Breakpoint in Philadelphia–positive (Ph+) Acute Lymphocytic Leukemia," Erikson et al, *PNAS, USA*, vol. 83, Mar. 1986, pp. 1807–1811.

Cremer et al, "Rapid Metaphase and Interphase Detection of Radiation–Induced Chromosome Aberrations in Human Lymphocytes by Chromosomal Suppression In Situ Hybridization," *Cytometry*, vol. 11, 1990, pp. 110–118.

Bookstein et al, "Human Retinoblastoma Susceptibility Gene: Genomic Organization and Analysis of Heterozygous Intragenic Deletion Mutants," *PNAS (USA)*, vol. 85, Apr. 1988, pp. 2210–2214.

Cohen et al, "Hereditary Renal–Cell Carcinoma Associated with a Chromosomal Translocation," *N. Engl. J. Med.*, vol. 301, No. 11, Sep. 1979, pp. 592–595.

Trask et al, "The Proximity of DNA Sequences in Interphase Cell Nuclei Is Correlated to Genomic Distance and Permits Ordering of Cosmids Spanning 250 Kilobase Pairs," *Genomics*, vol. 5, 1989, pp. 710–717.

McCormick, "The Polymerase Chain Reaction and Cancer Diagnosis," *Cancer Cells*, vol. 1, No. 2, Oct. 1989, pp. 56–61.

Lawrence et al, "Sensitive, High–Resolution Chromatin and Chromosome Mapping *In Situ*: Presence and Orientation of Two Closely Integrated Copies of EBV in a Lymphoma Line," *Cell*, vol. 52, Jan. 1988, pp. 51–61.

Cremer et al, "Detection of Chromosome Aberrations in Metaphase and Interphase Tumor Cells by *in situ* Hybridization Using Chromosome–Specific Library Probes," *Human Genetics*, vol. 80, 1988, pp. 235–246.

Pinkel et al, "Detection of Structural Chromosome Aberrations in Metaphase Spreads and Interphase Nuclei by *in situ* Hybridization High Complexity Probes Which Stain Entire Human Chromosomes," *Am. J. Hum. Genet.* (Supplement) vol. 43, No. 3, Sep. 1988, p. A118 (Abstract 0471:11.5).

Lichter et al, "Delineation of Individual Human Chromosomes in Metaphase and Interphase Cells by *in situ* Suppression Hybridization Using Recombinant DNA Libraries," *Human Genet.*, vol. 80, 1988, pp. 224–234.

Collins and Weissman, "Directional cloning of DNA fragments at a large distance from an initial probe: A circularization method", *PNAS (USA)*, 81: 6812–6816 (Nov. 1984).

LeGrys et al, "Clinical Applications of DNA Probes in the Diagnosis of Genetic Diseases," *CRC Crit. Rev. Clin. Lab. Sci.*, vol. 25, No. 4, 1987, pp. 255–274.

Lichter et al, "Rapid Detection of Human Chromosome 21 Aberrations by *in situ* Hybridization," *PNAS USA*, vol. 85, Dec. 1988, pp. 9664–9668.

Pinkel et al, "Cytogenetic Analysis by *In Situ* Hybridization with Fluorescently Labeled Nucleic Acid Probes," *Cold Spring Harbor Symposia on Quantitative Biology*, vol. Ll, 1986, pp. 151–157.

Pinkel et al, "Genetic Analysis by Quantitative Microscopy and Flow Cytometry Using Fluorescence In Situ Hybridization with Chromosome–Specific Nucleic Acid Probes," *Am. J. Hum. Genet.* (Supplement), vol. 39, No. 3, Sep. 1986, p. A129 (379).

Pinkel et al, "Cytogenetic Analysis During Leukemia Therapy Using Fluorescence *in situ* Hybridization with Chromosome–Specific Nucleic Acid Probes," *Am. J. Hum. Genet.* (Supplement), vol. 41, No. 3, Sep. 1987, p. A34 (096; 12.12).

Pinkel et al, "Simplified Cytogenetics Using Biotin Labeled Nucleic Acid Probes and Quantitative Fluorescence Microscopy," *Am. J. Hum. Genet.* (Supplement), vol. 37, No. 4, Jul. 1985, pp. A112 (328;17.2).

Pinkel et al, "Simplified Cytogenetics Using Biotin Labeled Nucleic Acid Probes and Quantitative Fluorescence Microscopy," *Am. J. Hum. Genet.* (Supplement), vol. 37, No. 4, Jul. 1985, pp. A112 (328;17.2).

Cremer et al, "Detection of Chromosome Aberrations in the Human Interphase Nucleus by Visualization of Specific Target DNAs with Radioactive and Non-Radioactive *in situ* Hybridization Techniques: Diagnosis of Trisomy 18 with Probe L1.84," *Hum. Genet.*, vol. 74, 1986, pp. 346–352.

OTHER PUBLICATIONS

Cremer et al, "Rapid Interphase and Metaphase Assessment of Specific Chromosomal Changes in Neuroectodermal Tumor Cells by in Situ Hybridization with Chemically Modified DNA Probes," *Exp. Cell Res.*, Vol. 176, 1988, pp. 199–220

Selypes et al, "A Noninvasive Method for Determination of the Sex and Karyotype of the Fetus from the Maternal Blood," *Hum. Genet.*, Vol. 79, 1988, pp. 357–359

Fuscoe et al, "An Efficient Method for Selecting Unique-Sequence Clones from DNA Libraries and Its Application To Fluorescent Staining of Human Chromosome 21 Using in Situ Hybridization," *Genomics*, vol. 5, 1989, pp. 100–109.

Devilee et al, "Detection of Chromosome Aneuploidy in Interphase Nuclei from Human Primary Breast Tumors Using Chromosome-specific Repetitive DNA Probes," *Cancer Res.*, vol. 48, Oct. 1988, pp. 5825–5830.

Friend et al, "A Human DNA Segment with Properties of the Gene that Predisposes to Retinoblastoma and Osteosarcoma," *Nature*, vol. 323, Oct. 16, 1986, pp. 643–646.

Nederlof et al, "Detection of Chromosome Aberrations in Interphase Tumor Nuclei by Nonradioactive In Situ Hybridizations," *Cancer Genet. Cytogenet.*, vol. 42, 1989, pp. 87–98.

Sparkes et al, "Regional Assignment of Genes for Human Esterase D and Retinoblastoma in Chromosome Band 13q14," *Science*, vol. 208, May 30, 1988, pp. 1042–1044.

Trent et al, "Report of the Committee on Structural Chromosome Changes in Neoplasia," *Cytogenet. Cell Genet.*, vol. 51, 1989, pp. 533–562.

Lichter et al, "High-Resolution Mapping of Human Chromosome 11 by in Situ Hybridization with Cosmid Clones," *Science*, vol. 247, Jan. 5, 1990, pp. 64–69.

Arnoldus et al, "Detection of the Philadelphia Chromosome in Interphase Nuclei (With 2 Color Plates)," *Cytogenet. Cell Genet.*, vol. 54, 1990, pp. 108–111.

Bergerheim et al, "Deletion Mapping in Human Renal Cell Carcinoma," *Cancer Res.*, vol. 49, Mar. 1989, pp. 1390–1396.

Kievits et al, "Direct Nonradioactive In Situ Hybridization of Somatic Cell Hybrid DNA to Human Lymphocyte Chromosomes," *Cytometry*, vol. 11, 1990, pp. 105–109.

Pinkel et al, "Fluorescence in situ Hybridization with Human Chromosome-Specific Libraries: Detection of Trisomy 21 and Translocations of Chromosome 4," *PNAS (USA)*, vol. 85, Dec. 1988, pp. 9138–9142.

Lichter et al, "Is Non-Isotopic in situ Hybridization Finally Coming of Age?," *Nature*, vol. 345, May 1990, pp. 93–94.

Gray et al, "Fluorescence Hybridization to Human Chromosome 21 Using Probes From A Charon 21 A Library," *Cytometry*, (Suppl. 1), 1987, Abst. 19, p. 4.

Bar-Am et al, "Detection of Amplified DNA Sequences in Human Tumor Cell Lines by Fluorescence In Situ Hybridization," *Genes, Chromosomes & Cancer*, vol. 4, 1982, pp. 314–320.

Roelofs et al, "Gene Amplification in Human Cells May Involve Interchromosomal Transposition and Persistence of the Original DNA Region," *The New Biologist*, vol. 4, No. 1, (Jan. 1992), pp. 75–86.

Smith et al, "Distinctive Chromosomal Structures Are Formed Very Early in the Amplification of CAD Genes in Syrian Hamster Cells," *Cell*, vol. 63, (Dec. 21, 1990), pp. 1219–1227.

Trask et al, "Early Dihydrofolate Reductase Gene Amplification Events in CHO Cells Usually Occur on the Same Chromosome Arm as the Original Locus," *Genes & Development*, vol. 3, (1989), pp. 1913–1925.

Windle et al, "A Central Role for Chromosome Breakage in Gene Amplification, Deletion Formation, and Amplicon Integration," *Genes & Development*, vol. 5, (1991), pp. 160–174.

METHODS FOR CHROMOSOME-SPECIFIC STAINING

The United States Government has rights in this invention pursuant to Contract No. W-7405-ENG-48 between the U.S. Department of Energy and the University of California, for the operation of Lawrence Livermore National Laboratory.

RELATED APPLICATION

This application is a continuation of U.S. Ser. No. 06/937,793, filed Dec. 4, 1986, now abandoned, which, in turn, is a continuation in part of U.S. Ser. No. 819,314, filed Jan. 16, 1986, now abandoned The prior applications were filed by the inventors named herein and were assigned to the same assignee. Priority is hereby claimed in said prior filed applications.

BACKGROUND OF THE INVENTION

The invention relates generally to the field of cytogenetics, and more particularly, to methods for identifying and classifying chromosomes.

Chromosome abnormalities are associated with genetic disorders, degenerative diseases, and exposure to agents known to cause degenerative diseases, particularly cancer, German, "Studying Human Chromosomes Today," *American Scientist*, Vol. 58, pgs. 182-201 (1970); Yunis, "The Chromosomal Basis of Human Neoplasia," *Science*, Vol. 221, pgs. 227-236 (1983); and German, "Clinical Implication of Chromosome Breakage," in *Genetic Damage in Man Caused by Environmental Agents*, Berg, Ed., pgs. 65-86 (Academic Press, New York, 1979). Chromosomal abnormalities can be of three general types: extra or missing individual chromosomes, extra or missing portions of a chromosome, or chromosomal rearrangements. The third category includes translocations (transfer of a piece from one chromosome onto another chromosome), and inversions (reversal in polarity of a chromosomal segment).

Detectable chromosomal abnormalities occur with a frequency of one in every 250 human births. Abnormalities that involve deletions or additions of chromosomal material alter the gene balance of an organism and generally lead to fetal death or to serious mental physical defects. Down's syndrome is caused by having three copies of chromosome 21 instead of the normal 2. This syndrome is an example of a condition caused by abnormal chromosome number, or aneuploidy. Chronic myelogeneous leukemia is associated with the exchange of chromosomal material between chromosome 9 and chromosome 22. The transfer of chromosomal material in this leukemia is an example of a translocation. Clearly, a sensitive method for detecting chromosomal abnormalities would be a highly useful tool for genetic screening.

Measures of chromosome breakage and other aberrations caused by ionizing radiation or chemical mutagens are widely used as quantitative indicators of genetic damage caused by such agents, *Biochemical Indicators of Radiation Injury in Man* (International Atomic Energy Agency, Vienna, 1971); and Berg, Ed. *Genetic Damage in Man Caused by Environmental Agents* (Academic Press, New York, 1979). A host of potentially carcinogenic and teratogenic chemicals are widely distributed in the environment because of industrial and agricultural activity. These chemicals include pesticides, and a range of industrial wastes and by-products, such as halogenated hydrocarbons, vinyl chloride, benzene, arsenic, and the like, Kraybill et al., Eds., *Environmental Cancer* (Hermisphere Publishing Corporation, New York, 1977). Sensitive measures of chromosomal breaks and other abnormalities could form the basis of improved dosimetric and risk assessment methodologies for evaluating the consequences of exposure to such occupational and environmental agents.

Current procedures for genetic screening and biological dosimetry involve the analysis of karyotypes. A karyotype is a collection of indices which characterize the state of an organism's chromosomal complement. It includes such things as total chromosome number, copy number of individual chromosome types (e.g., the number of copies of chromosome X), and chromosomal morphology, e.g., as measured by length, centromeric index, connectedness, or the like. Chromosomal abnormalities can be detected by examination of karyotypes. Karyotypes are determined by staining an organism's metaphase, or condensed, chromosomes. Metaphase chromosomes are used because, until recently, it has not been possible to visualize nonmetaphase, or interphase chromosomes due to their dispersed condition in the cell nucleus.

The metaphase chromosomes can be stained by a number of cytological techniques to reveal a longitudinal segmentation into entities generally referred to as bands. The banding pattern of each chromosome within an organism is unique, permitting unambiguous chromosome identification regardless of morphological similarity, Latt, "Optical Studies of Metaphase Chromosome Organization," *Annual Review of Biophysics and Bioengineering*, Vol. 5, pgs. 1-37 (1976). Adequate karyotyping for detecting some important chromosomal abnormalities, such as translocations and inversions requires banding analysis. Unfortunately, such analysis requires cell culturing and preparation of high Quality metaphase spreads, which is extremely difficult and time consuming, and almost impossible for tumor cells.

The sensitivity and resolving power of current methods of karyotyping, are limited by the lack of stains that can readily distinguish different chromosomes having highly similar staining characteristics because of similarities in such gross features as size, morphology, and/or DNA base composition.

In recent years rapid advances nave taken place in the study of chromosome structure and its relation to genetic content and DNA composition. In part, the progress has come in the form of improved methods of gene mapping based on the availability of large quantities of pure DNA and RNA fragments for probes produced by genetic engineering techniques, e.g., Kao, "Somatic Cell Genetics and Gene Mappings," *International Review of Cytology*, Vol. 85, pgs. 109-146 (1983), and D'Eustachio et al., "Somatic Cell Genetics in Gene Families," Science, Vol. 220, pgs. 9, 19-924 (1983). The probes for gene mapping comprise labeled fragments of single stranded or double stranded DNA or RNA which are hybridized to complementary sites on chromosomal DNA. The following references are representative of studies utilizing gene probes for mapping: Harper et al. "Localization of the Human Insulin Gene to the Distal End of the Short Arm of Chromosome 11," *Proc. Natl. Acad. Sci.*, Vol. 78, pgs. 4458-4460; Kao et al., "Assignment of the Structural Gene Coding for Albumin to Chromosome 4," Human Genetics, Vol. 62, pgs. 337-341 (1982); Willard et al., "Isolation and Characterization of a Major Tandem Repeat Family from the Human X Chromosome," *Nucleic Acids Research*, Vol. 11, pgs. 2017-2033 (1983); and Falkow et al., U.S. Pat. No. 4,358,535, issued 9 Nov. 1982, entitled "Specific DNA Probes in Diagnostic Microbiology." The hybridization process involves unravelling, or melting, the double stranded nucleic acids by heating, or other means. This step in the hybridization process is sometimes referred to as denaturing the nucleic acid. When the mixture of probe and target nucleic acids cool, strands having complementary bases recombine, or anneal. When a probe anneals with a target nucleic acid, the probe's location on the target can be detected by a label carried by the probe. When the target nucleic acid remains in its natural biological setting, e.g., DNA in chromosomes or cell nuclei (albeit fixed or altered by preparative techniques) the hybridization process is referred to as in situ hybridization.

Use of hybridization probes has been limited to identifying the location of genes or known DNA sequences on chromosomes. To this end it has been crucially important to produce pure, or homogeneous, probes to minimize hybridizations at locations other than at the site of interest, Henderson, "Cytological Hybridization to Mammalian Chromosomes," *International Review of Cytology*, Vol. 76, pgs. 1–46 (1982).

Manuelidis et al., in "Chromosomal and Nuclear Distribution of the Hind III 1.9-KB Human DNA Repeat Segment," *Chromosoma*, Vol. 91, pgs. 28-38 (1984), disclose the construction of a single kind of DNA probe for detecting multiple loci on chromosomes corresponding to members of a family of repeated DNA sequences.

Wallace et al., in "The Use of Synthetic Oligonucleotides as Hybridization Probes. II. Hybridization of Oligonucleotides of Mixed Sequence to Rabbit Beta-Globin DNA, "Nucleic Acids Research, Vol. 9, pgs. 879-894 (1981), disclose the construction of synthetic Oligonucleotide probes having mixed base sequences for detecting a single locus corresponding to a structural gene. The mixture of base sequences was determined by considering all possible nucleotide sequences which could code for a selected sequence of amino acids in the protein to which the structural gene corresponded.

Olsen et al., in "Isolation of Unique Sequence Human X Chromosomal Deoxyribonucleic Acid," *Biochemistry*, Vol. 19, pgs. 241 9-2428 (1980), disclose a method for isolating labeled unique sequence human X chromosomal DNA by successive hybridizations: first, total genomic human DNA against itself so that a unique sequence DNA fraction can be isolated; second, the isolated unique sequence human DNA fraction against mouse DNA so that homologous mouse/human sequences are removed; and finally, the unique sequence human DNA not homologous to mouse against the total genomic DNA of a human/mouse hybrid whose only human chromosome is chromosome X, so that a fraction of unique sequence X chromosomal DNA is isolated.

SUMMARY OF THE INVENTION

The invention includes methods and compositions for staining chromosomes. In particular, chromosome specific staining reagents are provided which comprise heterogeneous mixtures of labeled nucleic acid fragments having substantial portions of substantially complementary base sequences to the chromosomal DNA for which specific staining is desired. The nucleic acid fragments of the heterogenous mixtures include double stranded or single stranded RNA or DNA. Heterogeneous in reference to the mixture of labeled nucleic acid fragments means that the staining reagents comprise many copies each of fragments having different base compositions and/or sizes, such that application of the staining reagent to a chromosome results in a substantially uniform distribution of fragments hybridized to the chromosomal DNA.

"Substantial proportions" in reference to the basic sequences of nucleic acid fragments that are complementary to chromosomal DNA means that the complementarity is extensive enougn so that the fragments form stable hybrids with the chromosomal DNA under standard hybridization conditions for the size and complexity of the fragment. In particular, the term comprehends the situation where the nucleic acid fragments of the heterogeneous mixture possess regions having non-complementary base sequences.

As discussed more fully below, preferably the heterogeneous mixtures are substantially free from so-called repetitive sequences, both the tandem variety and the interspersed variety (see Hood et al., *Molecular Biology of Eucaryotic Cells* (Benjamin/Cummings Publishing Company, Menlo Park, Calif., 1975) for an explanation of repetitive sequences). Hood et al. states at pages 47-48 that "[e]ucaryotic sequences can be divided somewhat arbitrarily into three general frequency classes, termed highly repetitive (also called satellite DNA), middle-repetitive, and unique." Hood et al. indicates at page 49 that "[h]ighly repetitive DNA sequences are located in regions of centromeric heterochromatin", and at page 50 that "[m]iddle-repetitive sequences are interspersed among unique sequences."

Tandem repeats are so named because they are clustered or contiguous on the DNA molecule which forms the backbone of a chromosome. Members of this class of repeats are also associated with well-defined regions of the chromosome, e.g., the centromeric region. Thus, if these repeats form a sizable fraction of a chromosome, and are removed from the heterogeneous mixture of fragments employed in the invention, perfect uniformity of staining may not be possible. This situation is comprehended by the use of the term "substantially uniform" in reference to the heterogeneous mixture of labeled nucleic acid fragments of the invention.

It is desirable to disable the hybridization capacity of repetitive sequences because copies occur on all the chromosomes of a particular organism; thus, their presence reduces the chromosome specificity of the staining reagents of the invention. As discussed more fully below hybridization capacity can be disabled in several ways, e.g., selective removal or screening of repetitive sequences from chromosome specific DNA, selective blocking of repetitive sequences by pre-reassociation with complementary fragments, or the like.

Preferably, the staining reagents of the invention are applied to interphase or metaphase chromosomal DNA by in situ hybridization, and the chromosomes are identified or classified, i.e., karyotyped, by detecting the presence of the label on the nucleic acid fragments comprising the staining reagent.

The invention includes chromosome staining reagents for the total genomic complement of chromosomes, staining reagents specific to single chromosomes, staining reagents specific to subsets of chromosomes, and staining reagents specific to subregions within a single chromosome. The term "chromosome-specific," is understood to encompass all of these embodiments of the staining reagents of the invention. The term is also understood to encompass staining reagents made from both normal and abnormal chromosome types.

A preferred method of making the staining reagents of the invention includes isolating chromosome-specific DNA, cloning fragments of the isolated chromosome-specific DNA to form a heterogeneous mixture of nucleic acid fragments, disabling the hybridization capacity of repeated sequences in the nucleic acid fragments, and labeling the nucleic acid fragments to form a heterogeneous mixture of labeled nucleic acid fragments. As described more fully below, the ordering of the steps for particular embodiments varies according to the particular means adopted for carrying out the steps.

The preferred method of isolating chromosome-specific DNA for cloning includes isolating specific chromosome types by fluorescence-activated sorting.

The present invention addresses problems associated with karyotyping chromosomes, especially for diagnostic and dosimetric applications. In particular, the invention overcomes problems which arise because of the lack of stains that are sufficiently chromosome-specific by providing reagents comprising heterogeneous mixtures of labeled nucleic acid fragments that-can be hybridized to the DNA of specific Chromosomes, specific subsets of chromosomes, or specific subregions of specific chromosomes. The staining technique of the invention opens up the possibility of rapid and highly sensitive detection of chromosomal abnormalities in both metaphase and interphase cells using standard clinical and laboratory equipment. It has direct application in genetic screening, cancer diagnosis, and biological dosimetry.

BRIEF DESCRIPTION OF THE DRAWINGS

FIG. 1b is a binary image of fluorescein staining of the same human metaphase spread as FIG. 1a.

DETAILED DESCRIPTION OF THE INVENTION

Figure 1A:
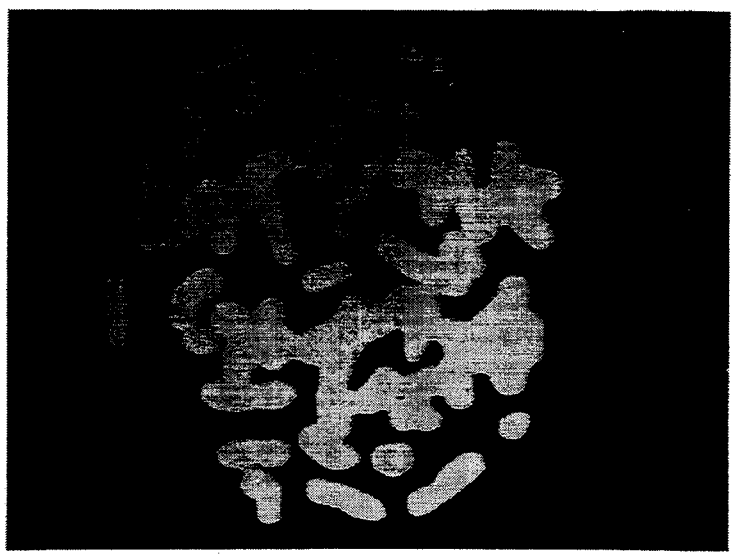
FIG. 1a is a binary image of a DAPI (4,6-diamidino-2-phenylindole, stained human metaphase spread.

The present invention includes compositions for staining individual chromosome types and methods for making and using the compositions. The compositions comprise heterogeneous mixtures of labeled nucleic acid fragments. The individual labeled nucleic acid fragments making up the heterogeneous mixture are essentially standard hybridization probes. That is, each chromosome-specific staining composition of the invention can be viewed as a large collection of hybridization probes to unique sequence regions of a specific chromosome. In fact, the preferred method of making the compositions of the invention entails generating a heterogeneous mixture on a fragment-by-fragment basis by isolating, cloning chromosomal DNA, and selecting from the clones hybridization probes to unique sequence regions of a particular chromosome. The precise number of distinct labeled nucleic acid fragments, or probes, comprising a heterogeneous mixture is not a critical feature of the invention. However, in particular applications, a trade-off may nave to be established between the number of distinct fragments in a heterogeneous mixture and the degree of nonspecific background staining: Where the tendency for nonspecific background staining is nigh, giving rise to low signal to noise ratios, it may De necessary to reduce the number of distinct fragments comprising the heterogeneous mixture. On the other hand, where nonspecific background staining is low, the number of distinct fragments may be increased. Preferably, the numbers of distinct fragments in a heterogeneous mixture is as high as possible (subject to acceptable signal to noise ratios) so that staining appears continuous over the body of the chromosomes.

Another constraint on the number of distinct fragments in the heterogeneous mixture is solubility. Upper bounds exist with respect to the fragment concentration, i.e., unit length of nucleic acid per unit volume, that can be maintained in solution. Thus, if fragments of a given average length are used at a given concentration (fragment per volume), then the number of different such fragments that can comprise the heterogeneous mixture is limited.

In one preferred embodiment where the heterogeneous mixture is generated on a fragment-by-fragment basis, the chromosomal DNA is initially cloned in long sequences, e.g., 35–45 kilobases in cosmids, or like vector. After amplification the inserts are cut into smaller fragments and labeled for formation to a heterogeneous mixture. In this embodiment, the chromosomal binding sites of the fragments are clustered in the chromosomal regions complementary to the cloned "parent" nucleic acid sequence. Fluorescent signals from such clusters are more readily detected than signals from an equivalent amount of label dispersed over the entire chromosome. In this embodiment, the clusters are substantially uniformly distributed over the chromosome.

Repetitive sequences, repeated sequences and repeats are used interchangeably throughout.

I. Isolation of Chromosome-Specific DNA and Formation of DNA Fragment Libraries.

The first step in the preferred method of making the compositions of the invention is isolating chromosome-specific DNA. This step includes first isolating a sufficient quantity of the particular chromosome type to which the staining composition is directed, then extracting the DNA from the isolated chromosomes. Here "sufficient quantity" means sufficient for carrying out subsequent steps of the method. Preferably, the extracted DNA is used to create a chromosome-specific library of DNA inserts which can be cloned using standard genetic engineering techniques. The cloned inserts are then isolated and treated to disable the hybridization capacity of repeated sequences. In this case, "sufficient quantity" means enough for the particular method used in constructing the DNA insert library.

Several methods are available for isolating particular chromosome types. For example, a technique for isolating human chromosome types involves forming hybrid cell lines from human cells and rodent cells, particularly mouse or hamster cells, e.g., see Kao, "Somatic Cell Genetics and Gene Mapping," *International Review of Cytology*. Vol. 85, pgs. 109–146 (1983), for a review. Human chromosomes are preferentially lost by the hybrid cells so that hybrid cell lines containing a full complement of rodent chromosomes and a single human chromosome can be selected and propagated, e.g., Gusella et al., "Isolation and Localization of DNA Segments from Specific Human Chromosomes," *Proc. Natl Acad Sci.*, Vol. 77, pgs. 2829–2833 (1980). Chromosome specific DNA can then be isolated by techniques disclosed by Schmeckpeper et al., "Partial Purification and Characterization of DNA from Human X Chromosome," *Proc. Natl Acad Sci.*, Vol. 76, pgs. 6525-6528 (1979); or Olsen et al., "Isolation of Unique Sequence Human X Chromosomal Deoxyribonucleic Acid," *Biochemistry*, Vol. 19, pgs. 2419-2428 (1980). Accordingly, these references are incorporated by reference. Briefly, sheared total human DNA is hybridized against itself on hydroxyapatite under conditions that allow elution of substantially pure unique sequence total human DNA from the hydroxyapatite. The unique sequence total human DNA is then reassociated and nick translated to add a label (see Maniatis et al., *Molecular Cloning A Laboratory Manual*, Cold Spring Harbor Laboratory, 1982, pgs. 109-112, for a description of the nick translation technique to add radioactive labels; and Brigato et al., "Detection of Viral Genomes in Cultured Cells and Paraffin-Embedded Tissue Sections Using Biotin-Labeled Hybridization Probes," *Virology*, Vol. 126, pgs. 32-50 (1982) for a description of the nick translation technique to add a biotin label). Poly(dA) tails are then synthesized to the 3' hydroxyl termini of the unique sequence DNA by incubating with terminal transferase under appropriate conditions. The poly(dA) unique human DNA is then hybridized against rodent DNA to remove homologous sequences. The nonhomologous poly(dA) unique human DNA is then hybridized against the total DNA of the human/rodent hybrid on hydroxyapatite; double stranded DNA is isolated. (This is the chromosome-specific unique sequence human DNA.) The poly(dA) tail is used to separate the labeled unique sequence DNA from the unlabeled unique sequences by binding the poly(dA) tails to oligo(dT) cellulose.

The preferred means for isolating particular chromosome types is by direct flow sorting of metaphase chromosomes with or without the use of interspecific hybrid cell systems. Direct sorting is preferred because there is considerable DNA sequence homology between rodent and human DNA, which necessitates additional hybridization steps (e.g., see Olsen et al., cited above), and the hybrid cell lines tend to be unstable with respect to retention of the human chromosomes.

For some species, every chromosome can be isolated by currently available sorting techniques. Most, but not all, human chromosomes are currently isolatable by flow sorting, Carrano et al., "Measurement and Purification of Human Chromosomes by Flow Cytometry and Sorting," *Proc. Natl. Acad. Sci.*, Vol. 76, pgs. 1382-1384 (1979). Thus, for isolation of some human chromosomes, use of the human/rodent hybrid cell system may be necessary. Chromosome sorting can be done by commercially available fluorescence-activated sorting machines, e.g., Becton Dickinson FACS-II or like instrument.

DNA is extracted from the isolated chromosomes by standard techniques, e.g., Marmur, "A Procedure for the Isolation of Deoxyribonucleic Acid from Micro-Organisms," *J. Mol. Biol.*, Vol. 3, pgs. 208-218 (1961); or Maniatis et al., *Molecular Cloning: A Laboratory Manual* (Cold Spring Harbor Laboratory, 1982)pgs. 280-281. These references are incorporated by reference for their descriptions of DNA isolation techniques.

Generation of insert libraries from the isolated chromosome-specific DNA is carried out using standard genetic engineering techniques, e.g., Davies et al., "Cloning of a Representative Genomic Library of the Human X Chromosome After Sorting by Flow Cytometry," *Nature*, Vol. 293, pgs. 374-376 (1981 ); Krumlauf et al., "Construction and Characterization of Genomic Libraries from Specific Human Chromosomes," *Proc. Natl. Acad. Sci.*, Vol. 79, pgs. 2971-2975 (1982); Lawn et al., "The Isolation and Characterization of Linked Delta-and-Beta-Globin Genes from a Cloned Library of Human DNA." *Cell*, Vol. 15, pgs. 1157-1174 (1978); and Maniatis et al., *"Molecular Cloning: A Laboratory Manual,"* (Cold Springs Harbor Laboratory, 1982), pgs. 256-308, the cited pages of Maniatis et al. and Lawn et al. being incorporated by reference.

In some cases, it is preferable that the nucleic acid fragments of the heterogeneous mixture consist of single-stranded RNA or DNA. The binding efficiency of single stranded nucleic acid probes has been found to be higher during in situ hybridization, e.g., Cox et al., "Detection of mRNAs in Sea Urchin Embryos by In Situ Hybridization Using Asymmetric RNA Probes," *Developmental Biology*, Vol. 101, pgs. 485-502 (1984). Standard methods are used to generate RNA fragments from isolated DNA fragments. For example, a method developed by Green et al., described in *Cell*, Vol. 32, pgs. 681-694 (1983), is commercially available from Promega Biotec (Madison, Wis.) under the tradename "Riboprobe." Other transcription kits suitable for use with the present invention are available from United States Biochemical Corporation (Cleveland, Ohio) under the tradename "Genescribe." Single stranded DNA probes can be produced with the single stranded bacteriophage M13, also available in kit form, e.g. Bethesda Research Laboratories (Gaithersburg, Md.).

II. Disabling the Hybridization Capacity of Repetitive Sequences.

As mentioned above, it is desirable to disable the hybridization capacity of repetitive sequences by removal, block, or like means. Repetitive sequences are distributed throughout the genome; most are not chromosome-specific. Consequently, in spite of the fact that the nucleic acid fragments of the invention are derived from isolated chromosomes, the presence of repeats greatly reduces the degree of chromosome-specificity of the staining reagents of the invention, particularly in genomes containing a significant fraction of repetitive sequences, such as the human genome.

Several techniques are available for disabling the hybridization capacity of repetitive sequences. Highly repetitive DNA sequences can be removed from the extracted chromosome-specific DNA by denaturing and incubating the extracted DNA against itself or against repetitive sequence-enriched total genomic DNA on hydroxyapatite, or like absorbent, at low $C_0t$ values, followed by fractionation of double stranded DNA from single stranded DNA.

Hydroxyapatite chromatography is a standard technique for fractionating DNA on the basis of reassociation conditions such as temperature, salt concentration, or the like. It is also useful for fractionating DNA on the basis of reassociation rate at fixed reassociative conditions, or stringencies. Materials for hydroxyapatite chromotography are available commercially, e.g., Bio-Rad Laboratories (Richmond, Calif.).

Fractionation based on resistance to $S_1$ nuclease can also be used to separate single stranded from double stranded DNA after incubation to particular $C_0t$ values. See Britten et al. "Analysis of Repeating DNA Sequences by Reassociation," in *Methods in Enzymology*, Vol. 29, pgs. 363-418 (1974), for an explanation of $C_0t$ values. Preferably, this initial reassociation step is carried out after the extracted chromosome-specific DNA has been broken into pieces and amplified by cloning.

One embodiment of the invention is obtained by labeling the fragments of the single stranded fraction eluted from the hydroxyapatite in the initial reassociation step. The particular $C_ot$ values required to separate middle repetitive and highly repetitive sequences from the chromosome-specific DNA may vary from species to species because of inter-specific differences in the fraction of the genomic DNA comprising middle and highly repetitive sequences. Most preferably in this embodiment, the initial reassociation step is to a $C_ot$ value in the range of about a few hundred to a few thousand.

In addition to self hybridization or hybridization against repetitive-sequence-enriched total genomic DNA, removal of repeats from fragment mixtures can also be accomplished by hybridization against immobilized nigh molecular weight total genomic DNA, following a procedure described by Brison et al., "General Method for Cloning Amplified DNA by Differential Screening with Genomic Probes," *Molecular and Cellular Biology*, Vol. 2, pgs. 578–587 (1982). Accordingly, this reference is incorporated by reference. Briefly, the procedure removed repeats from fragment mixtures in the size range of a few tens of bases to a few hundred bases. Minimally sheared total genomic DNA is bound to diazonium cellulose, or like support. The fragment mixture is then hydrized against the immobilized DNA to $C_ot$ values in the range of about 1 to 100. The preferred stringency of the hybridization conditions may vary depending on the base composition of the DNA.

The preferred means for disabling hybridization capacity is selecting unique sequence nucleic acid inserts from a chromosome-specific DNA library. For example, following Benton and Davis, "Screening Lambda gt Recombinant Clones by Hybridization to Single Plaques in situ," *Science*, Vol. 196, pgs. 180–182 (1977), pieces of chromosome-specific DNA are inserted into lambda gt bacteriophage or like vector. The phages are plated on agar plates containing a suitable host bacteria. DNA from the resulting phage plaques is then transferred to a nitrocellulose filter by contacting the filter to the agar plate. The filter is then treated with labeled repetitive DNA so that phage plaques containing repetitive sequence DNA can be identified. Those plaques that do not correspond to labeled spots on the nitrocellulose filter comprise clones which may contain unique sequence DNA. Clones from these plaques are selected and amplified, radioactively labeled, and hybridized to Southern blots of genomic DNA which has been digested with the same enzyme used to generate the inserted chromosome-specific DNA. Clones carrying unique sequence inserts are recognized as those that produce a single band during Southern analysis.

Another method of disabling the hybridization capacity of repetitive DNA sequences within nucleic acid fragments involves blocking the repetitive sequences by pre-reassociation of fragments with fragments of repetitive-sequence-enriched DNA, by pre-reassociation of the target DNA with fragments of repetitive-sequence-enriched DNA, or pre-reassociation of both the fragments of the heterogeneous mixture and the target DNA with repetitive-sequence-enriched DNA. The method is generally described by Sealy et al., "Removal of Repeated Sequences from Hybridization Probes," *Nucleic Acid Research*, Vol. 13, pgs. 1905–1922 (1985), which reference is incorporated by reference.

The term pre-reassociation refers to a hybridization step involving the reassociation of unlabeled, repetitive DNA or RNA with the nucleic acid fragments of the heterogeneous mixture just prior to the in situ hybridization step, or with the target DNA either just prior to or during the in situ hybridization step. This treatment results in nucleic acid fragments whose repetitive sequences are blocked by complementary fragments such that sufficient unique sequence regions remain free for attachment to chromosomal DNA during the in situ hybridization step.

III. Labeling the Nucleic Acid Fragments of the Heterogeneous Mixture.

Several standard techniques are available for labeling single and double stranded nucleic acid fragments of the heterogeneous mixture. They include incorporation of radioactive labels, e.g. Harper et al. *Chromosoma*, Vol. 83, pgs. 431–439 (1981); direct attachment of fluorescent labels, e.g. Smith et al., *Nucleic Acids Research*, Vol. 13, pgs. 2399–2412 (1985), and Connolly et al., *Nucleic Acids Research*, Vol. 13, pgs. 4485–45(92 (1985); and various chemical modifications of the nucleic acid fragments that render them detectable immunochemically or by other affinity reactions, e.g. Tchen et al., "Chemically Modified Nucleic Acids as Immunodetectable Probes in Hybridization Experiments," *Proc. Natl. Acad. Sci.*, Vol 81, pgs. 3466–3470 (1984); Richardson et al., "Biotin and Fluorescent Labeling of RNA Using T4 RNA Ligase," *Nucleic Acids Research*, Vol. 11, pgs. 6167–6184 (1983); Langer et al., "Enzymatic Synthesis of Biotin-Labeled Polynucleotides: Novel Nucleic Acid Affinity Probes," *Proc. Natl. Acad. Sci.*, Vol. 78, pgs. 6633–6637 (1981); Brigati et al., "Detection of Viral Genomes in Cultured Cells and Paraffin-Embedded Tissue Sections Using Biotin-Labeled Hybridization Probes," *Virology*, Vol 126, pgs. 32–50 (1 983); Broker et al., "Electron Microscopic Visualization of tRNA Genes with Ferritin-Avidin: Biotin Labels," *Nucleic Acids Research*, Vol. 5, pgs. 363–384 (1978); Bayer et al., "The Use of the Avidin Biotin Complex as a Tool in Molecular Biology," *Methods of Biochemical Analysis*, Vol. 26, pgs. 1–45 (1980) and Kuhlmann, *Immunoenzyme Techniques in Cytochemistry* (Weinheim, Basel, 1984).

All of the labeling techniques disclosed in the above references may be preferred under particular circumstances. Accordingly, the above-cited references are incorporated by reference. Several factors govern the choice of labeling means, including the effect of the label on the rate of hybridization and binding of the nucleic acid fragments to the chromosomal DNA, the accessibility of the bound probe to labeling moieties applied after initial hybridization, the nature and intensity of the signal generated by the label, the expense and ease in which the label is applied, and the like.

The term labeled nucleic acid fragment as used herein comprehends labeling means which include chemical modification of nucleic acid fragment by substituting derivatized bases, by forming adducts, or the like, which after hybridization render the nucleic acid fragments detectable by immunochemical stains or affinity labels, such as biotin-avidin labeling systems, N-acetoxy-N-2-acetylaminofluorene (AFF) labeling systems, or the like.

For most applications, labeling means which generate fluorescent signals are preferred.

IV. In Situ Hybridization.

Application of the heterogeneous mixture of the invention to chromosomes is accomplished by standard in situ hybridization techniques. Several excellent guides to the technique are available, e.g., Gall an d Pardue, "Nucleic Acid Hybridization in Cytological Preparations," *Methods in Enzymology*, Vol. 21, pgs. 470–480 (1981); Henderson, "Cytological Hybridization to Mammalian Chromosomes," *International Review of Cytology*, Vol. 76, pgs. 1–46 (1982); and Angerer, et al., "In Situ Hybridization to Cellular RNAs," in *Genetic Engineering: Principles and Methods*, Setlow and Hollaender, Eds., Vol. 7, pgs. 43–65 (Plenum Press, New York, 1985). Accordingly, these references are incorporated by references.

Three factors influence the staining sensitivity of a heterogeneous mixture of hybridization probes: (1) efficiency of hybridization (fraction of target DNA that can be hybridized by probe), (2) detection efficiency (i.e., the amount of visible signal that can be obtained from a given amount of hybridization probe), and (3) level of noise produced by nonspecific binding of probe or components of the detection system.

Generally in situ hybridization comprises the following major steps: (1) fixation of tissue or biological structure to be examined, (2) prehybridization treatment of the biological structure to increase accessibility of target DNA, and to reduce nonspecific binding, (3) hybridization of the heterogeneous mixture of probe to the DNA in the biological structure or tissue; (4) posthybridization washes to remove probe not bound in specific hybrids, and (5) detection of the hybridized probes of the heterogeneous mixture. The reagents used in each of these steps and their conditions of use vary depending on the particular chromosomes being stained.

The following comments are meant to serve as a guide for applying the general steps listed above. Some experimentation may be required to establish optimal staining conditions for particular applications.

Fixatives include acid alcohol solutions, acid acetone solutions, Petrunkewitsch's reagent, and various aldehydes such as formaldehyde, paraformaldehyde, glutaraldehyde, or the like. Preferably, ethanol-acetic acid or methanol-acetic acid solutions in about 3:1 proportions are used to fix the chromosomes. For cells or chromosomes in suspension, the fixation procedure disclosed by Trask, et al., in *Science*, Vol. 230, pgs. 1401–1402 (1985), is preferred. Accordingly, Trask, et al., is incorporated by reference. Briefly, $K_2CO_3$ and dimethylsuberimidate (DMS) are added (from a 5x concentrated stock solution, mixed immediately before use) to a suspension containing about $5 \times 10^6$ nuclei/ml. Final $K_2CO_3$ and DMS concentrations are 20 mM and 3 mM, respectively. After 15 minutes at 25° C., the pH is adjusted from 10.0 to 8.0 by the addition of 50 microliters of 100 mM citric acid per milliliter of suspension. Nuclei are washed once by centrifugation (300 g, 10 minutes 4° C. in 50 mM kCl, 5 mM Hepes buffer, at pH 9.0, and 10 mM $MgSO_4$).

Preferably, before application of the stain, chromosomes are treated with agents to remove proteins. Such agents include enzymes or mild acids. Pronase or proteinase K are the preferred enzymes. Optimization of deproteinization requires a combination of protease concentration and digestion time that maximize hybrization, but does not cause unacceptable loss of morphological detail. Optimum conditions vary according to chromosome types and method of fixation. Thus, for particular applications, some experimentation may be required to optimize protease treatment.

Proteins can al so be removed by mild acid extraction e.g., 0.02–0.2N HCl followed by high temperature (e.g., 70° C.) washes.

In some cases pretreatment with RNase may be desirable to remove residual RNA from the fixed chromosomes. Such removal can be accomplished by incubation of chromosomes in 50–100 microgram/milliliter RNase the fixed in $2 \times$ SSC (where SSC is a solution of 0.15M NaCL and 0.015M sodium citrate) for a period of 1–2 hours at room temperature.

The step of hybridizing the probes of the heterogeneous mixture to the chromosomal DNA involves (1) denaturing the chromosomal DNA so that probes can gain access to complementary single stranded regions, and (2) applying the heterogeneous mixture under conditions which allow the probes to anneal to complementary sites. Methods for denaturation include incubation in the presence of high pH, low pH, nigh temperature, or organic solvents such as formamide, tetraalkylammonium halides, or the like, at various combinations of concentration and temperature. The preferred denaturing procedure is incubation for between about 1–10 minutes in formamide at a concentration between about 35–95 percent in $2 \times X$ SSC and at a temperature between about 25°–70° C. Determination of the optimal incubation time, concentration, and temperature within these ranges depends on several variables, including the method of fixation and chromosome type.

After the chromosomal DNA is denatured, the denaturing agents are removed before application of the heterogeneous mixture. Where formamide and neat are the primary denaturing agents, removal is conveniently accomplished by plunging the substrate or vessel containing the denatured chromosomes into an ice bath, and/or by several washes by an ice-cold solvent, such as a 70%, 80%, 95% cold ethanol series.

The ambient physiochemical conditions of the chromosomal DNA at the time the heterogeneous mixture is applied is referred to herein as the hybridization conditions, or annealing conditions. Optimal hybridization conditions for particular applications depend on several factors, including salt concentration, incubation time of chromosomes in the heterogeneous mixture, and the concentrations, complexities, and lengths of the probes making up the heterogeneous mixture. Roughly, the hybridization conditions must be sufficiently denaturing to minimize nonspecific binding and hybridizations with excessive numbers of base mismatches. On the other hand, the conditions cannot be so stringent as to reduce hybridizations below detectable levels or to require excessively long incubation times. Generally, the hybridization conditions are much less stringent than the conditions for denaturing the chromosomal DNA.

The concentrations of probes in the heterogeneous mixture is an important variable. The concentrations must be high enough so that the respective chromosomal binding sites are saturated in a reasonable time (e.g., within about 18 hours), yet concentrations higher than that just necessary to achieve saturation should be avoided so that nonspecific binding is minimized. A preferred concentration range of nucleic acid fragments in the heterogeneous mixture is between about 1–10 nanograms per kilobase of complexity per milliliter.

The fixed chromosomes can be treated in several ways either during or after the hybridization step to reduce nonspecific binding of probe DNA. Such treatments include adding a large concentration of non-probe, or "carrier", DNA to the heterogeneous mixture, using coating solutions, such as Dennardt's solution (*Biochem. Biophys. Res. Commun.*, Vol. 23, pgs. 641–645 (1966), with the heterogeneous mixture, incubating for several minutes, e.g., 5–20, in denaturing solvents at a temperature 5°–10° C. above the hybridization temperature, and in the case of RNA probes, mild treatment with single strand RNase (e.g., 5–10 micrograms per millileter RNase) in 2×SSC at room temperature for 1 hour).

V. Making and Using a Staining Reagent Specific to Human Chromosome 21.

A. Isolation of Chromosome 21 and Construction of a Chromosome 21-Specific Library DNA fragments from human chromosome-specific libraries are available from the National Laboratory Gene Library Project through the American Type Culture Collection (ATCC), Rockville, Md. Chromosome 21-specific DNA fragments were generated by the procedure described by Fuscoe et al., in "Construction of Fifteen Human Chromosome-Specific DNA Libraries from Flow-Purified Chromosomes, *Cytogentic Cell Gentics*, Vol. 43, pgs. 79–86 (1986), which reference is incorporated by reference. Briefly, a human diploid fibroblast culture was established from newborn foreskin tissue. Chromosomes of the cells were isolated by the $MgSO_4$ method for van den Engh et al., *Cytometery*, Vol. 5, pgs. 108–123 (1984), and stained with the fluorescent dyes. Hoechst 33258 and Chromomycin A3. Chromsome 21 was purified on the Lawrence Livermore National Laboratory high speed sorter, described by Peters et al., *Cytometry*, Vol. 6, pgs. 290–301 (1985).

After sorting, chromosome concentrations were approximately $4 \times 10^5$/ml. Therefore, prior to DNA extraction, the chromosomes ($0.2-1.0 \times 10^6$) were concentrated by centrifugation at $40{,}000 \times g$ for 30 minutes at 4° C. The pellet was then resuspended in 100 microliters of DNA isolation buffer (15 mM NaCl 10 mM EDTA, 10 mM Tris HCl pH 8.0) containing 0.5% SDS and 100 micrograms/ml proteinase K. After overnight incubation at 37° C., the proteins were extracted twice with phenol:chloroform:isoamyl alcohol (25:24:1) and once with chloroform:isoamyl alcohol (24:1). Because of the small amounts of DNA, each organic phase was reextracted with a small amount of 10 mM Tris pH 8.0, 1 mM EDTA (TE). Aqueous layers were combined and transferred to a Schleicher and Schuell mini-collodion membrane (#UH020/25) and dialyzed at room temperature against TE for 6–8 hours. The purified DNA solution was then digested with 50 units of Hind III (Bethesda Research Laboratories, Inc.) in 50 mM NaCl 10 mM Tris HCl pH 7.5, 10 mM $MgCl_2$, 1 mM dithiothreitol. After 4 hours at 37°, the reaction was stopped by extractions with phenol and chloroform as described above. The acqueous phase was dialyzed against water overnight at 4° C. in a mini-collodion bag and then 2 micrograms of Charon 21A arms cleaved with Hind III and treated with calf alkaline phosphatase (Boehringer Mannheim) were added. This solution was concentrated under vacuum to a volume of 50–100 microliters and transferred to a 0.5 ml microfuge tube where the DNA was precipitated with one-tenth volume 3M sodium acetate pH 5.0 and 2 volumes ethanol. The precipitate was collected by centrifugation, washed with cold 70% ethanol, and dissolved in 10 microliters of TE.

After allowing several hours for the DNA to dissolve, 1 microliter of 10X ligase buffer (0.5M Tris HCl pH 7.4, 0.1 M $MgCl_2$, 0.1M dithiothreitol, 10 mM ATP, 1 mg/ml bovine serum albumin) and 1 unit of T4 ligase (Bethesda Research Laboratory, Inc.) were added. The ligation reaction was incubated at 10° C. for 16–20 hours and 3 microliters aliquots were packaged into phage particles using *in vitro* extracts prepared from *E. coli* strains BHB 2688 and BHB 2690, described by Hohn in *Methods in Enzymology*, Vol. 68, pgs. 299–309 (1979) *Molecular Cloning: A Laboratory Manual*, (Cold Spring Harbor Laboratory, New York, 1982). Briefly, both extracts were prepared by sonication and combined at the time of in vivo packaging. These extracts packaged wild-type lambda DNA at an efficiency of $1-5 \times 10^8$ plaque forming units (pfu) per microgram. The resultant phage were amplified on *E. coli* LE392 at a density of approximately $10^4$ pfu/150 mm dish for 8 hours to prevent plaques from growing together and to minimize differences in growth rates of different recombinants. The phage were eluted from the agar in 10 ml SM buffer (50 mM Tris HCl pH 7.5, 10 mM $MgSO_4$, 100 mM NaCl 0.01% gelatin) per plate by gentle snaking at 4° C. for 12 hours. The plates were then rinsed with an additional 4 ml of SM. After pelleting cellular debris, the phage suspension was stored over chloroform at 4° C.

B. Construction and Use of Chromsome 21-Specific Stain for Staining Chromosome 21 of Human Lymphocytes Clones having unique sequence inserts are isolated by the method of Benton and Davis, *Science*, Vol. 196, pgs. 180–182 (1977). Briefly, about 1000 recombinant phage are isolated at random from the chromosome 21-specific library. These are transferred to nitrocellulose and probed with nick translated total genomic human DNA.

Of the clones which do not show strong hybridization, approximately 300 are picked which contain apparent unique sequence DNA. After the selected clones are amplified, the chromosome 21 insert in each clone is $^{32}p$ labeled and hybridized to Southern blots of human genomic DNA digested with the same enzyme used to construct the chromosome 21 library, i.e., Hind III. Unique sequence containing clones are recognized as those that produce a single band during Southern analysis. Roughly, 100 such clones are selected for the heterogeneous mixture. The unique sequence clones are amplified, the inserts are removed by Hind III digestions, and the inserts are separated from the phage arms by gel electrophoresis. The probe DNA fragments (i.e., the unique sequence inserts) are removed from the gel and biotinylated by nick translation (e.g., by a kit available from Bethesda Research Laboratories). Labeled DNA fragments are separated from the nick translation reaction using small spin columns made in 0.5 ml Eppendorph tubes filled with Sephadex G-50 (medium) swollen in 50 mM Tris, 1 mM EDTA, 0.1% SDS, at pH 7.5. Human lymphocyte chromosomes are prepared following Harper et al, *Proc. Natl. Acad. Sci.*, Vol. 78, pgs. 4458–4460 (1981). Metaphase and interphase cells were washed 3 times in phosphate buffered saline, fixed in methanol-acetic acid (3:1) and dropped onto cleaned microscope slides. Slides are stored in a nitrogen atmosphere at −20° C.

Slides carrying interphase cells and/or metaphase spreads are removed from the nitrogen, heated to 65° C. for 4 hours in air, treated with RNase (100 micrograms/ml for 1 hour at 37° C.), and dehydrated in an ethanol series. They are then treated with proteinase K (60 ng/ml at 37° C. for 7.5 minutes) and dehydrated. The proteinase K concentration is adjusted depending on the cell type and enzyme lot so that almost no phase microscopic image of the chromosomes remains on the dry slide. The hybridization mix consists of (final concentrations) 50 percent formamide, 2X SSC, 10 percent dextran sulfate, 500 micrograms/ml carrier DNA (sonicated herring sperm DNA), and 2.0 microgram/ml biotin-labeled chromsome 21-specific DNA. This mixture is applied to the slides at a density of 3 microliters/cm under a glass cover slip and sealed with rubber cement. After overnight incubation at 37° C., the slides are washed at 45° C. (50% formamide-2X SS pH 7, 3 times 3 minutes; followed by 2X SSC pH 7, 5 times 2 minutes) and immersed in BN buffer (0.1M Na bicarbonate, 0.05 percent NP-40, pH 8). The slides are never allowed to dry after this point.

The slides are removed from the BN buffer and blocked for 5 minutes at room temperature with BN buffer containing 5% non-fat dry milk (Carnation) and 0.02% Na Azide (5 microliter/cm$^2$ under plastic coverslips). The coverslips are removed, and excess liquid briefly drained and fluorescein-avidin DCS (3 microgram/ml in BN buffer with 5% milk and 0.02% NaAzide) is applied (5 microliter/cm$^2$). The same coverslips are replaced and the slides incubated 20 minutes at 37° C. The slides are then washed 3 times for 2 minutes each in BN buffer at 45° C. The intensity of biotin-linked fluorescence is amplified by adding a layer of biotinylated goat anti-avidin antibody (5 microgram/ml in BN buffer with 5% goat serum and 0.02% NaAzide), followed, after washing as above, by another layer of fluorescein-avidin DCS. Fluorescein-avidin DCS, goat antiavidin and goat serum are all available commercially, e.g., Vector Laboratories (Burlingame, Calif.). After washing in BN, a fluorescence antifade solution, p-phenylenediamine (1.5 microliter/cm$^2$ of coverslip) is added before observation. It is important to keep this layer thin for optimum microscopic imaging. This antifade significantly reduced fluorescein fading and allows continuous microscopic observation for up to 5 minutes. The DNA counterstains (DAPI or propidium iodide) are included in the antifade at 0.25–0.5 microgram/mi.

The red-fluorescing DNA-specific dye propidium iodide (PI) is used to allow simultaneous observation of hybridized probe and total DNA. The fluorescein and PI are excited at 450–490 nm (Zeiss filter combination 487709). Increasing the excitation wavelength to 546 nm (Zeiss filter combination 487715) allows observation of the PI only. DAPI, a blue fluorescent DNA-specific stain excited in the ultraviolet (Zeiss filter combination 487701), is used as the counterstain when biotin-labeled and total DNA are observed separately. Metaphase chromosome 21s are detected by randomly located spots of yellow distributed over the body of the chromosome.

VI. Chromosome 21-Specific Staining by Blocking Repetitive Probe and Chromosomal DNA High concentrations of unlabeled human genomic DNA and lambda phage DNA were used to inhibit the binding of repetitive and vector DNA sequences to the target chromosomes. Heavy proteinase digestion and subsequent fixation improved access of probes to target DNA.

Human metaphase spreads were prepared on microscope slides with standard techniques and stored immediately in a nitrogen atmosphere at −20° C.

Slides were removed from the freezer and allowed to warm to room temperature in a nitrogen atmosphere before beginning the staining procedure. The warmed slides were first treated with 0.6 microgram/ml proteinase K in P buffer (20 mM Tris, 2 mM CaCl$_2$ at pH 7.5) for 7.5 minutes, and washed once in P buffer. The amount of proteinase K used needs to be adjusted for the particular enzyme lot and cell type. Next the slides were washed once in paraformaldehyde buffer (phosphate buffered saline (PBS) plus 50 mM MgCl$_2$, at pH 7.5), immersed for 10 minutes in 4% paraformaldehyde in paraformaldehyde buffer, and washed once in 2X SSC (0.3M NaCl, 0.03 M sodium citrate at pH 7). DNA on the slides was denatured by immersing in 70% formamide and 2X SSC at 70° C. for 2 minutes. After denaturing the slides were stored in 2X SSC. A hybridization mix was prepared which consisted of 50% formamide, 10% dextran sulfate, 1% Tween 20, 2X SSC, 0.5 mg/ml human genomic DNA, 0.03 mg/ml lambda DNA, and 3 microgram/ml biotin labeled probe DNA. The probe DNA consisted of the highest density fraction of phage from the chromosome 21 Hind III fragment library (ATCC accession number 57713), as determined by a cesium chloride gradient. (Both insert and phage DNA of the probe were labeled by nick translation.) The average insert size (amount of chromosome 21 DNA), as determined by gel electrophoresis is about 5 kilobases. No attempt was made to remove repetitive sequences from the inserts or to isolate the inserts from the lambda phage vector. The hybridization mix was denatured by heating to 70° C. for 5 minutes followed by incubation at 37° C. for 1 hour. The incubation allows the human genomic DNA and unlabeled lambda DNA in the hybridization mix to block the human repetitive sequences and vector sequences in the probe.

Figure 1B:
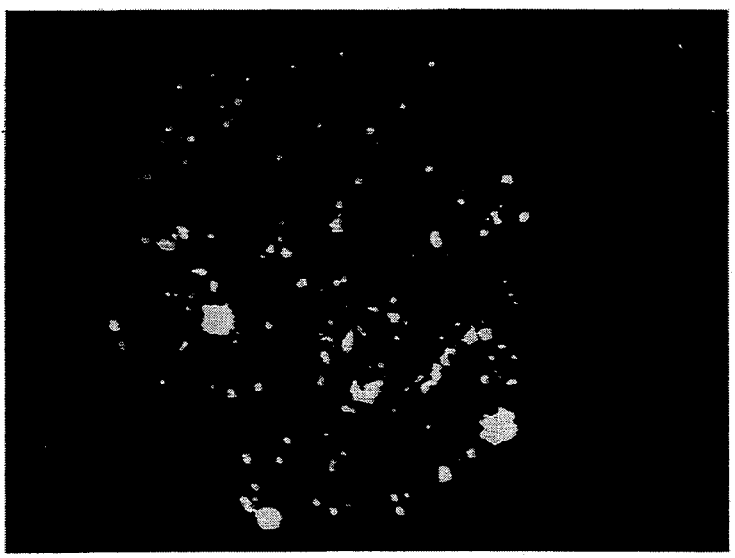
Figure 1C:
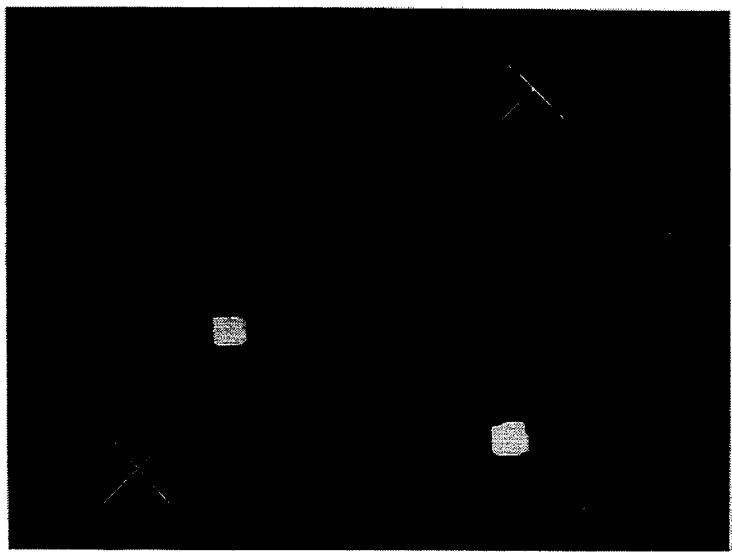
FIG. 1c is a binary image of the chromosome 21s alone, nonspecifically stained objects having been removed by standard image processing techniques.

The slide containing the human metaphase spread was removed from the 2X SSC and blotted dry with lens paper. The hybridization mix was immediately applied to the slide, a glass cover slip was placed on the slide with rubber cement, and the slide was incubated overnight at 37° C. Afterwards preparation of the slides proceeded as described in Section V (wherein chromosome 21 DNA was stained with fluorescein and total chromosomal DNA counterstained with DAPI). FIGS. 1a–c illustrate the results. FIG. 1a is a DAPI image of the human metaphase spread obtained with a computerized image analysis system. It is a binary image showing everything above threshold as white, and the rest as black. The primary data was recorded as a gray level image with 256 intensity levels. (Small arrows indicate the locations of the chromosome 21S.) FIG. 1b is a fluorescein image of the same spread as in FIG. 1a, again in binary form. (Again, small arrows indicate the locations of the chromosome 21s.) FIG. 1c illustrates the positions of the chromosome 21s with other less densely stained objects removed standard by image processing techniques.

The descriptions of the foregoing embodiments of the invention nave been presented for purpose of illustration and description. They are not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

We claim:

1. A method of staining target chromosomal DNA comprising:
   (a) providing 1) labeled nucleic acid that comprises fragments which are substantially complementary to nucleic acid segments within the chromosomal DNA for which detection is desired, and 2) blocking nucleic acid that comprises fragments which are substantially complementary to repetitive segments in the labeled nucleic acid; and
   (b) employing said labeled nucleic acid, blocking nucleic acid, and chromosomal DNA in in situ hybridization so that labeled repetitive segments are substantially blocked from binding to the chromosomal DNA, while hybridization of unique segments within the labeled nucleic acid to the chromosomal DNA is allowed, wherein blocking of the labeled repetitive segments is sufficient to permit detection of hybridized labeled nucleic acid containing unique segments, and wherein the chromosomal DNA is present in a morphologically identifiable chromosome or cell nucleus during the in situ hybridization.

2. The method of claim 1 wherein the blocking nucleic acid is hybridized with the labeled nucleic acid prior to hybridization of the labeled nucleic acid with the chromosomal DNA.

3. The method of claim 1 wherein the blocking nucleic acid is hybridized with the chromosomal DNA prior to hybridization of the labeled nucleic acid with the chromosomal DNA.

4. The method of claim 1 wherein the blocking nucleic acid is hybridized with the labeled nucleic acid and separately with the chromosomal DNA prior to hybridization of the labeled nucleic acid with the chromosomal DNA.

5. The method of claim 1 wherein the labeled nucleic acid, the blocking nucleic acid, and the chromosomal DNA are hybridized together during in situ hybridization step.

6. The method of claim 1 wherein the labeled nucleic acid comprises fragments which are designed to allow detection of extra or missing chromosomes, extra or missing portions of a chromosome, or chromosomal rearrangements.

7. The method of claim 6 wherein the chromosomal rearrangement is a translocation or an inversion.

8. The method of claim 6 wherein the labeled nucleic acid is designed to allow detection of a chromosomal rearrangement consistent with chronic myelogenous leukemia.

9. The method of claim 6 wherein the labeled nucleic acid is designed to allow detection of aneuploidy.

10. The method of claim 6 wherein the extra chromosome is chromosome 21.

11. The method of claim 1 wherein the labeled nucleic acid comprises fragments complementary to the total genomic complement of chromosomes, fragments complementary to a single chromosome, fragments complementary to a subset of chromosomes, or fragments complementary to a subregion of a single chromosome.

12. The method of claim 11 wherein the fragments are selected from the nucleic acid of normal human chromosomes 1 through 22, X, and Y.

13. The method of claim 1 wherein the chromosomal DNA is metaphase or interphase chromosomal DNA.

14. The method of claim 1 wherein the repetitive segments comprise segments which are substantially complementary to highly repetitive segments and middle-repetitive segments.

15. The method of claim 14 wherein the repetitive segments are substantially complementary to satellite repetitive segments.

16. The method of claim 14 wherein the repetitive segments are substantially complementary to tandem repetitive segments or repetitive segments located in regions of centromeric heterochromatin.

17. The method of claim 14 wherein the repetitive segments are substantially complementary to interspersed repetitive segments.

* * * * *